United States Patent [19]

Warner, Jr. et al.

[11] Patent Number: 4,666,896

[45] Date of Patent: May 19, 1987

[54] CHLORHEXIDINE SALTS AND COMPOSITIONS OF SAME

[75] Inventors: Paul L. Warner, Jr., Clarence; Grey B. Kornegay, East Amherst; George Redl, Buffalo, all of N.Y.

[73] Assignee: Bristol-Myers Company, New York, N.Y.

[21] Appl. No.: 734,250

[22] Filed: May 14, 1985

Related U.S. Application Data

[63] Continuation of Ser. No. 487,715, Apr. 28, 1983, abandoned, which is a continuation of Ser. No. 255,599, Apr. 20, 1981, abandoned, which is a continuation-in-part of Ser. No. 211,169, Nov. 28, 1980, abandoned, which is a continuation of Ser. No. 33,593, Apr. 26, 1979, abandoned.

[51] Int. Cl.$^4$ .................. A61K 31/66; C07C 87/00
[52] U.S. Cl. ..................... 514/114; 514/300; 514/635; 260/501.21; 260/502.5 R
[58] Field of Search ............... 514/114, 300; 260/501.21, 502.5 R

[56] References Cited

U.S. PATENT DOCUMENTS

| | | | |
|---|---|---|---|
| 3,442,938 | 5/1969 | Christensen et al. | 260/502.5 |
| 3,590,036 | 6/1971 | Lesher et al. | 260/240 |
| 3,689,480 | 9/1972 | Christensen et al. | 260/239.75 |
| 3,689,673 | 9/1972 | Phares | 424/326 |
| 3,694,447 | 9/1972 | Pagano | 260/279 R |
| 3,751,562 | 8/1973 | Nichols | 424/45 |
| 3,888,782 | 6/1975 | Boghosian | 252/106 |
| 3,932,607 | 1/1976 | Hesselgren | 424/52 |

FOREIGN PATENT DOCUMENTS

1108532  4/1968  United Kingdom .

OTHER PUBLICATIONS

Quesnel et al., Journal of Applied Bact. 45, pp. 397-405 (1978).
Doke et al., Antibiotics & Chemotherapy, 8, (7), pp. 342-348 (1958).
Richards et al., J. of Pharmacy & Pharmacology, 24th Supp., 159-160 (1972).
Richards et al., Pharm. Journal, 210, 118-120 (1973).
Clarke et al.—Med. J. of Australia, 1971, 446 (1971).
Clarke—Med. J. of Australia, 1975, 1, 413-5 (1975).
Lowbury et al., British Med. J., 1, 493-6 (1976).

Primary Examiner—Leonard Schenkman
Attorney, Agent, or Firm—David M. Morse

[57] ABSTRACT

The dinalidixate and diphosphanilate salts of chlorhexidine possess antibacterial activity. They exhibit synergism as compared with comparable concentrations of chlorhexidine and the respective free acid. Synergistic compositions comprising a mixture of a chlorhexidine salt with phosphanilic acid or a salt of phosphanilic acid, or with nalidixic acid, or a salt of nalidixic acid are disclosed. Dermatological compositions of such novel salts, and all such mixtures, are provided.

5 Claims, No Drawings

CHLORHEXIDINE SALTS AND COMPOSITIONS OF SAME

DESCRIPTION

The application is a continuation of Ser. No. 487,715, filed Apr. 28, 1983 which is a continuation of Ser. No. 255,599, filed Apr. 20, 1981, which is a continuation-in-part of Ser. No. 211,169, filed Nov. 28, 1980, which is a continuation of Ser. No. 033,593, filed Apr. 26, 1979, all now abandoned.

TECHNICAL FIELD

The present invention relates to antibacterial compounds of the formula:

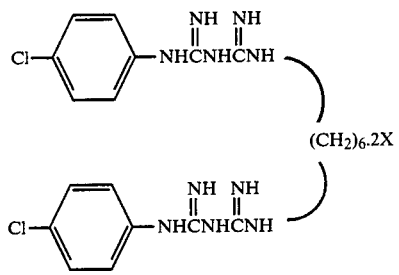

wherein X is selected from the group consisting of nalidixic acid and phosphanilic acid, and compositions containing same. The invention also encompasses mixtures of chlorhexidine salts and nalidixic acid or a salt thereof or phosphanilic acid or a salt thereof. More particularly, the invention relates to certain novel chlorhexidine salts, antibacterial dermatological compositions containing such salts, and certain mixtures of chlorhexidine and nalidixic acid, nalidixic salts, phosphanilic acid or phosphanilic salts.

The novel salts comprise chlorhexidine dinalidixate and chlorhexidine diphosphanilate. Preferably, the chlorhexidine diphosphanilate is employed as a hydrate or partial hydrate.

BACKGROUND ART

Chlorhexidine, nalidixic acid and phosphanilic acid are known in the art. Moreover, as shown in U.S. Pat. Nos. 3,960,745, issued June 1, 1976, and 3,855,140, issued Dec. 17, 1974, certain chlorhexidine salts are likewise known. Such salts include the hydrochloride, gluconate, isethionate, formate, acetate, glutamate, succinamate, monodiglycolate, dimethanesulphonate, lactate, di-isobutyrate and the glucoheptonate.

Polyhydroxycarboxylic acid salts of biguanides, such as, for example, chlorhexidine di-D-gluconate, are disclosed in U.S. Pat. No. 2,990,425, issued June 27, 1961, as being highly soluble in water.

The oral antibacterial use of water soluble salts of chlorhexidine, such as the gluconate, acetate, fluoride, dihydrogen fluoride and the dihydrogen chloride, is disclosed in U.S. Pat. No. 3,976,765, issued Aug. 24, 1976.

An oral antibacterial composition comprising a combination of dodecyl-di-(aminoethyl)glycine and chlorhexidine or its digluconate, diacetate, dichloride or monofluorophosphate salts is disclosed in U.S. Pat. No. 3,932,607, issued Jan. 13, 1976.

Salts of chlorhexidine with certain sequestering amino carboxylic acids are disclosed in U.S. Pat. No. 3,888,947, issued June 10, 1975. Preferred salts include, mono-chlorhexidine nitrilotriacetate, trichlorhexidine, di-[diethylene triaminepentaacetate], mono-chlorhexidine-di-[N,N-dihydroxyethylaminoacetate], mono-chlorhexidine N-hydroxyethylenediaminetriacetate and mono-chlorhexidine di-[N-hydroxyethylethylenediaminetriacetate]. Such sequestrates are disclosed to have greater antibacterial activity than the corresponding bisguanido salt (confer column 3, lines 22 through 42 of the patent).

Bis-guanide hydroxyalkane sulphonic acid salts are disclosed in British Patent Specification No. 815,800. Such salts (including the isethionic acid salt, the 2:3-dihydroxypropane-1-sulphonic acid salt, the 3-chloro-2-hydroxypropane-1-sulphonic acid salt and the 2-hydroxypropane-1-sulphonic acid salt) are asserted to advantageously possess high solubility in water.

U.S. Pat. No. 3,252,181, issued Oct. 6, 1964, discloses monobiguanides having at least one alkoxypropyl group having from about 11 to 19 carbon atoms attached to the $N^1$ or $N^5$ terminal nitrogen atoms. Such compounds are said to display exceptional antimicrobial activity and may be employed as the free base or, where water solubility is a factor in their use, as their salts with the inorganic and organic acids (such as mono and polycarboxylic and sulfur-containing mono and poly acids and acidic nitrogen compounds). Exemplary of acid salts are the hydrochloride, hydrobromide, sulfate, phosphate, borate, phosphite, sulfite, sulfonate, nitrite, carbonate, nitrate, acetate, tartrate, propionate, oxalate, maleate, malate, picrate and β-ethoxypropionate salts. Examples of suitable acidic nitrogen compounds are theophylline, substituted theophyllines and similar purines, saccharin, phthalimide, benzoxazine-2,4-diones, oxazolidine-2,4-dione and substituted oxazolidone-2,4-diones, N-p-methylbenzene sulfonyl-N'-n-butylurea, barbituric acids, mercaptobenzothiazole, 8-chlorotheophylline and succinimide. Patentees teach (at column 11, lines 36 through 70) that their monobiguanides can be employed with other medicaments.

As stated heretofore, nalidixic acid, phosphanilic acid and chlorhexidine are known in the art. The antibacterial agent, nalidixic acid (1-ethyl-1,4-dihydro-7-methyl-4-oxo-1,8-naphthyridine-3-carboxylic acid) is the subject of U.S. Pat. No. 3,590,036, issued June 29, 1971. Nalidixic acid has not to the instant inventors' knowledge been heretofore utilized topically.

Phosphanilic acid ($p-NH_2C_6H_4PO_3H_2$, 4-aminobenzene phosphonic acid) has been synthesized (inter alia Doak et al. JACS 74 (1952)) and found to be active against various organisms (see for example Kuhn et al., Ber. 75,711 (1942); Klotz et al., JACS 69,473 (1947); and Thayer et al., Antibiotics and Chemotherapy, 3,256 (1953)).

U.S. Pat. No. 3,159,537, issued Dec. 1, 1964, teaches that certain phosphonic acid compounds, including phosphanilic acid, increase the oral absorption (viz. increase blood level) of tetracycline antibiotics.

Complexes of phosphanilic acid and an aminoacridine compound (preferably, 9-amino, 3-amino or 6-amino acridine) are disclosed in U.S. Pat. Nos. 3,694,447, issued Sept. 26, 1972 and 3,794,723, issued Feb. 26, 1974, as having antibacterial and antifungal activity.

Phosphanilic acid has also been reported to show synergistic action with trimethoprim against a variety of bacteria (see U.S. Pat. No. 4,125,610, issued Nov. 14, 1978). It has also been reported to show synergistic action with neomycin and with streptomycin against Enterobacteriaceae (see Ciencia (Mexico) 17, 71-73 (1957)).

Finally, it should be noted that the topical anti-infective, chlorhexidine, (1,6-bis(N-p-chlorophenyl-diguanido)hexane) is long known to the prior art having been disclosed in U.S. Pat. No. 2,684,924, issued July 27, 1954.

DETAILED DESCRIPTION OF INVENTION

The novel antibacterial compounds of the formula

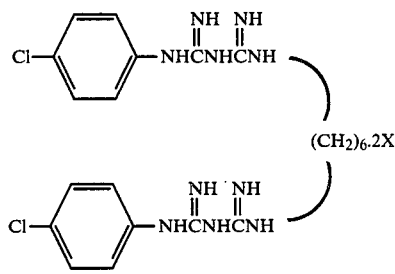

wherein X is selected from the group consisting of nalidixic acid and phosphanilic acid are readily prepared by for example reacting the desired acid, dissolved in suitable solvent therefor (preferably hot ethanol in the case of nalidixic acid and hot water in the case of phosphanilic acid) with chlorhexidine free base, dissolved in a suitable solvent, preferably hot ethanol or hot methanol.

The resultant precipitate is recovered, washed then recrystallized according to methods known per se whereby the desired novel salt of the present invention is obtained.

The following examples more fully illustrate the method of preparation of the novel salts of the present invention.

EXAMPLE 1

A solution of 505 mg. (1.0 mmole) of chlorhexidine free base in 50 ml. hot ethanol is cautiously added to a hot solution of 464 mg. (2.0 mmole) of nalidixic acid in 50 ml. hot ethanol. An immediate precipitate results and is filtered off after the mixture has cooled. The recovered precipitate is successively washed with ethanol, chloroform then ether. The washed solid precipitate is then recrystallized from dimethylformamide (DMF) whereby 0.6 g. (representing a yield of 61.9% of theoretical) of off-white solid chlorhexidine dinalidixate having a melting point of 224° to 226° C. is obtained. IR (KBr disc): bands at 3330–2860 (broad multiplet), 1625, 1492, 1445, 1252, 1132, 1092, 820 and 745 cm$^{-1}$.

Anal. Calc'd for $C_{46}H_{54}Cl_2N_{14}O_6$ C, 56.96; H, 5.61; N, 20.21; Cl, 7.31; O, 9.90. Found: C, 56.86; H, 5.74; N, 20.21; Cl, 7.25.

EXAMPLE 2

A warm solution of 505 mg. (1.0 mmole) of chlorhexidine free base in 50 ml. methanol is added to a solution of 346 mg. (1.0 mmole) of phosphanilic acid in 250 ml. of hot water. The resultant solution is then evaporated to approximately 50 ml. and cooled whereby a waxy solid separates. The waxy solid is filtered off, washed with water then recrystallized from water. After drying, 205 mg. of chlorhexidine diphosphanilate dihydrate, having a melting point of 172°–174° C., are produced. This represents a yield of 23.1% of theoretical. $\lambda_{max}^{EtOH}=255$ (Am=51,600) IR (KBr disc): bands at 3460 to 2930 (broad multiplet), 1650 to 1600 (broad multiplet), 1515, 1490, 1420, 1130 and 828 cm$^{-1}$.

Anal. Calc'd for $C_{34}H_{50}Cl_2N_{12}O_8P_2$ C, 45.99; H, 5.67; Cl, 7.98; N, 18.93; O, 14.42; P, 6.97. Found C, 45.94; H, 5.75; Cl, 8.25; N, 19.00; P, 6.85.

Chlorhexidine dinalidixate and chlorhexidine diphosphanilate produced in Examples 1 and 2, were tested for their activity in vitro against 32 strains of Pseudomonas aeruginosa, 26 strains of other gram-negative organisms and 18 gram-positive organisms. Minimum inhibitory concentration data for the reference standards, chlorhexidine digluconate, chlorhexidine diacetate, nalidixic acid and phosphanilic acid, were also obtained. Chlorhexidine base could not be employed as a reference as it is unstable. The results of the study are reported in Table I as follows:

TABLE I

| | | | Antibacterial Activity of Chlorhexidine Di Nalidixate and Chlorhexidine Di Phosphanilate Salts | | | | | |
|---|---|---|---|---|---|---|---|---|
| | | | (MIC (μg/ml)$^a$ | | | | | |
| | | Number | Chlorhexidine | | | | | |
| Organism | Gram Stain | of Strains | Nalidixic Acid Salt | Phosphanilic Acid Salt | Digluconate$^b$ | Diacetate$^b$ | Nalidixic Acid | Phosphanilic Acid |
| S. aureus | + | 6 | 6.4 | 4 | 4 | 2 | 44.8 | >125 |
| S. pneumoniae | + | 4 | 19 | 16 | 16 | 13.5 | >125 | >125 |
| S. pyogenes | + | 3 | 8 | 5 | 5 | 4 | >125 | >125 |
| S. viridans | + | 1 | 63 | 32 | 63 | 32 | 125 | >125 |
| Streptococcus (β-hemolytic) | + | 2 | 11.3 | 8 | 5.7 | 5.7 | >125 | >125 |
| S. faecalis | + | 2 | 16 | 8 | 8 | 5.7 | >125 | >125 |
| E. coli | − | 3 | 8 | 10 | 10 | 5 | 16 | 79.4 |
| K. pneumoniae | − | 2 | 2.8 | 88.7 | 63 | 32 | 11.3 | 32 |
| | | 1 | 8 | 63 | 32 | 32 | 16 | >125 |
| E. cloacae | − | 3 | 6.4 | 32 | 32 | 16 | 25.4 | >79.4 |
| P. mirabilis | − | 2 | 16 | 22.6 | 88.7 | 88.7 | 11.3 | 8 |
| | | 1 | 16 | 32 | >125 | >125 | 16 | 125 |
| P. morgaii | − | 2 | 2.8 | 22.6 | 16 | 5.7 | 8 | 44.7 |
| P. rettgeri | − | 1 | 1 | 63 | 63 | 32 | 2 | 32 |
| | | 2 | 11.3 | 11.3 | >125 | >125 | 11.3 | 1.4 |
| P. vulgaris | − | 2 | 2.8 | 8 | >125 | >89 | 4 | 2.8 |
| | | 1 | 16 | 16 | 125 | 125 | 16 | 63 |
| S. marcesceus | − | 3 | 4 | 1.3 | 50.3 | >125 | 6.4 | 0.5 |
| P. stuartii | − | 2 | 11.3 | 5.7 | 44.9 | 32 | 16 | 2.8 |
| | | 1 | 16 | 16 | 125 | >125 | 16 | 2 |

TABLE I-continued

| | | | Antibacterial Activity of Chlorhexidine Di Nalidixate and Chlorhexidine Di Phosphanilate Salts | | | | | |
|---|---|---|---|---|---|---|---|---|
| | | | (MIC (μg/ml)[a] | | | | | |
| | | Number | Chlorhexidine | | | | Nalidixic | Phosphanilic |
| | Gram | of | Nalidixic Acid | Phosphanilic Acid | | | Acid | Acid |
| Organism | Stain | Strains | Salt | Salt | Digluconate[b] | Diacetate[b] | | |
| P. aeruginosa | — | 26 | 48.6 | 3.2 | >125 | >125 | >125 | 1.5 |
| | | 5 | 42 | 72.5 | >125 | ~125 | >125 | 36.4 |
| | | 1 | 32 | 63 | 125 | 125 | >125 | >125 |

[a]Geometric mean MIC values where applicable
[b]In terms of chlorhexidine content The data of Table I shows that the dinalidixic acid salt of chlorhexidine is more effective than either nalidixic acid or chlorhexidine alone as against many of the strains tested. The data shows chlorhexidine dinalidixate to be particularly active against all strains of P. aeruginosa as well as against individual strains of K. pneumoniae, E. cloacae and P. morganii while chlorhexidine diphosphanilate is seen to be effective against 26 out of 32 strains of P. aeruginosa and a strain of P. mirabilis and P. vulgaris.

The results of Table I indicate that the nalidixic acid salt of chlorhexidine is more effective then either of its two components alone.

To more fully investigate the synergistic effect of the novel salts of the present invention, chlorhexidine dinalidixate and chlorhexidine diphosphanilite, as well as nalidixic acid, phosphanilic acid, chlorhexidine diacetate and a 1:1 mixture of chlorhexidine digluconate and nalidixic acid, were tested for activity in vitro against 30 strains of Pseudomonas aeruginosa, 23 strains of other gram-negative organisms. Minimum inhibitory concentrations of the novel salts of the instant invention as well as the reference standards (viz. chlorhexidine digluconate, chlorhexidine diacetate, nalidixic acid, phosphanilic acid and the 1:1 mixture of chlorhexidine digluconate and nalidixic acid) were obtained. In contrast to the procedure employed in obtaining the results of Table I, all compounds were tested on a straight weight basis and in a medium low in antibiotic antagonists (viz. Mueller-Hinton Broth+1% Ionagar), thus increasing antibiotic sensitivity.

The results, as reported in Table II which follows, show chlorhexidine dinalidixate to be more effective than either chlorhexidine or nalidixic acid, particularly against strains of Klebsiella pneumoniae, and Enterococcus cloacae and 28 of 30 strains of P. aeruginosa. The phosphanilic acid salt of chlorhexidine shows clear improvement over phosphanilic acid and chlorhexidine alone as against 4 of 30 strains of P. aeruginosa. The results also show chlorhexidine diphosphanilate to be a very effective antipseudomonal. It inhibits 29 of the 30 strains of P. aeruginosa at MIC values of 8 μg/ml or less as compared to chlorhexidine digluconate and diacetate, which inhibit only 2 strains below 8 μg/ml.

TABLE II

| | | | Antibacterial Activity of Various Salts of Chlorhexidine in Mueller-Hinton Broth Supplemented with 1% Ionagar | | | | | |
|---|---|---|---|---|---|---|---|---|
| | | | MIC (μg/ml)[a] | | | | | |
| | | | Chlorhexidine | | | | | |
| | | Number | Digluconate + | | | | | |
| | Gram | of | Nalidixic | | | | Nalidixic | Phosphanilic |
| Organism | Stain | Strains | Acid (1/1) | Nalidixate | Phosphanilate | Digluconate | Diacetate | Acid | Acid |
| S. aureus | + | 4 | 1.2 | 0.21 | 0.25 | 0.25 | 0.21 | 32 | >125 |
| S. pneumoniae | + | 3 | 99.5 | 12.7 | 10.1 | 10.1 | 6.4 | >125 | >125 |
| S. pyogenes | + | 3 | 16 | 4 | 3.2 | 3.2 | 3.2 | >125 | >125 |
| S. viridans | + | 1 | 63 | 16 | 16 | 16 | 8 | >125 | >125 |
| Streptococcus (β-hemolytic) | + | 2 | 16 | 4 | 4 | 1.4 | 1.4 | >125 | >125 |
| S. faecalis | + | 2 | 11.3 | 8 | 4 | 2 | 2 | >125 | >125 |
| E. coli | — | 3 | 1 | 0.63 | 0.63 | 0.63 | 0.32 | 2 | 32 |
| K. pneumoniae | — | 2 | 1.4 | 1 | 2.8 | 4 | 2.8 | 2.8 | 16 |
| | | 1 | 2 | 1 | 4 | 4 | 4 | 4 | >125 |
| E. cloacae | — | 1 | 1 | 1 | 4 | 4 | 1 | 4 | 16 |
| | | 2 | 1.4 | 1 | 2.8 | 2.8 | 1 | 4 | >125 |
| P. mirabilis | — | 3 | 6.4 | 4 | 4 | 12.7 | 8 | 4 | 3.2 |
| P. rettgeri | — | 1 | 0.5 | 0.5 | 1 | 8 | 4 | 0.25 | 1 |
| | | 3 | 5 | 4 | 6.4 | 16 | 8 | 2.5 | 1.3 |
| P. vulgaris | — | 1 | 4 | 1 | 4 | 2 | 1 | 0.5 | >125 |
| S. marcescens | — | 3 | 2.5 | 2.5 | 2 | 6.4 | 12.7 | 1.3 | 0.5 |
| P. stuartii | — | 2 | 4 | 2.8 | 2 | 4 | 2 | 2 | 2.8 |
| | | 1 | 8 | 4 | 4 | 16 | 16 | 4 | 4 |
| P. aeruginosa | — | 1 | 8 | 2 | 2 | 4 | 4 | 63 | 1 |
| | | 1 | 8 | 4 | 8 | 4 | 4 | 63 | 63 |
| | | 1 | 8 | 4 | 16 | 32 | 32 | 63 | >125 |
| | | 1 | 8 | 4 | 2 | 16 | 16 | >125 | 63 |
| | | 19 | 8.9 | 4.5 | 1.9 | 19.2 | 18.5 | 65.3 | 0.77 |
| | | 5 | 12.1 | 8 | 2.6 | 18.4 | 18.4 | >125 | 1.2 |
| | | 2 | 8 | 8 | 5.7 | 16 | 16 | 63 | 63 |

[a]geometric MIC values where applicable.
Inocula: The majority of cultures were diluted 1000-fold; all the streptococci, except S. faecalis were used undiluted.

To more fully amplify the unexpected synergism of the novel salts of the present invention the MIC values, reported in Tables I and II in μg/ml, were converted to MIC values of μmoles/ml using the following molecular formulae and molecular weights:

Chlorhexidine dinalidixate: $C_{46}H_{54}Cl_2N_{14}O_6$, 969.94.

Nalidixic acid: $C_{12}H_{12}N_2O_3$, 232.23.
Phosphanilic acid: $C_6H_8NO_3P$, 173.11.

Tables III and IV show the results of such conversion and enable a comparison of potencies on a more meaningful molecule to molecule basis rather than gram to gram basis.

TABLE III

Antibacterial Activity of Chlorhexidine as a Nalidixic Acid and Phosphanilic Acid Salt
MIC (μmoles/ml × $10^3$)

| Organism | Gram Stain | Number of Strains | Chlorohexidine Nalidixic Acid Salt | Chlorohexidine Phosphanilic Acid Salt | Digluconate | Diacetate | Nalidixic Acid | Phosphanilic Acid |
|---|---|---|---|---|---|---|---|---|
| S. aureus | + | 6 | 6.6 | 4.6 | 4.5 | 3.2 | 193 | >880 |
| S. pneumoniae | + | 4 | 19.6 | 18.6 | 17.8 | 21.5 | >539 | >880 |
| S. pyogenes | + | 3 | 8.2 | 5.8 | 5.6 | 6.4 | >539 | >880 |
| S. viridans | + | 1 | 64.9 | 37.3 | 70.1 | 51.1 | 539 | >880 |
| Streptococcus (β-hemolytic) | + | 2 | 11.6 | 9.3 | 6.3 | 9.1 | >539 | >880 |
| S. faecalis | + | 2 | 16.5 | 9.3 | 8.9 | 9.1 | >539 | >880 |
| E. coli | − | 3 | 8.2 | 11.7 | 11.1 | 8.0 | 68.9 | 559 |
| K. pneumoniae | − | 2 | 2.9 | 103.5 | 70.1 | 51.1 | 48.7 | 225 |
|  |  | 1 | 8.2 | 73.5 | 35.6 | 51.1 | 68.9 | >880 |
| E. cloacae | − | 3 | 6.6 | 37.3 | 35.6 | 25.6 | 109 | >559 |
| P. mirabilis | − | 2 | 16.5 | 26.3 | 98.8 | 141.6 | 48.7 | 56.3 |
|  |  | 1 | 16.5 | 37.3 | >139 | >200 | 68.9 | 880 |
| P. morganii | − | 2 | 2.9 | 26.3 | 17.8 | 9.1 | 34.4 | 315 |
| P. rettgeri | − | 1 | 1 | 73.5 | 70.1 | 51.1 | 8.6 | 225 |
|  |  | 2 | 11.6 | 13.0 | >139 | >200 | 48.7 | 9.8 |
| P. vulgaris | − | 2 | 2.9 | 9.3 | >139 | >142 | 17.2 | 19.7 |
|  |  | 1 | 16.5 | 18.6 | 139 | 200 | 68.9 | 444 |
| S. marcescens | − | 3 | 4 | 2 | 56 | >200 | 27.5 | 3.5 |
| P. stuartii | − | 1 | 11.6 | 6.6 | 50 | 51.1 | 68.9 | 19.7 |
|  |  | 2 | 16.5 | 18.6 | 139 | >200 | 68.9 | 14.1 |
| P. aeruginosa | − | 26 | 50.1 | 3.6 | >139 | >200 | >539 | 10.6 |
|  |  | 5 | 43.2 | 84.3 | >139 | 200 | >539 | 256 |
|  |  | 1 | 32.9 | 73.5 | 139 | 200 | >539 | >880 |

TABLE IV

Antibacterial Activity of Various Salts of Chlorhexidine in Mueller-Hinton Broth Supplemented with 1% Ionagar
MIC (μmole/ml × $10^3$)

| Organism | Gram Stain | Number of Strains | Chlorhexidine Digluconate + Nalidixic Acid (1:1) | Nalidixate | Phosphanilate | Digluconate | Diacetate | Nalidixic Acid | Phosphanilic Acid |
|---|---|---|---|---|---|---|---|---|---|
| S. aureus | + | 4 | 2.3 | 0.2 | 0.3 | 0.3 | 0.3 | 137 | >880 |
| S. pneumoniae | + | 3 | 193 | 13 | 11.7 | 11.2 | 10.2 | >539 | >880 |
| S. pyogenes | + | 3 | 31 | 4 | 3.7 | 3.5 | 5.1 | >539 | >880 |
| S. viridans | + | 1 | 122 | 1.6 | 18.6 | 17.8 | 12.7 | >539 | >880 |
| Streptococcus (β-hemolytic) | + | 2 | 31 | 21.9 | 8.2 | 4.6 | 2.2 | >539 | >880 |
| S. laecalis | + | 2 | 21.9 | 8.2 | 4.6 | 2.2 | 3.1 | >539 | >880 |
| E. coli | − | 3 | 1.9 | 0.6 | 0.7 | 0.7 | 0.5 | 8.6 | 225 |
| K. pneumoniae | − | 2 | 2.7 | 1 | 3.2 | 4.4 | 4.1 | 12 | 112 |
|  |  | 1 | 3.8 | 1 | 4.6 | 4.4 | 1.5 | 17.2 | >880 |
| E. cloacae | − | 1 | 1.9 | 1 | 4.6 | 4.4 | 1.5 | 17.2 | 112 |
|  |  | 2 | 2.7 | 1 | 3.2 | 3.1 | 12.7 | 17.2 | >880 |
| P. mirabilis | − | 3 | 12.4 | 4 | 4.6 | 14.1 | 6.4 | 17.2 | 22.5 |
| P. rettgeri | − | 1 | 0.9 | 0.5 | 1 | 8.9 | 12.7 | 1 | 7 |
|  |  | 3 | 9.7 | 4 | 7.4 | 17.8 | 1.5 | 10.7 | 9 |
| P. vulgaris | − | 1 | 7.7 | 1 | 4.6 | 2.2 | 20.3 | 2.1 | >880 |
| S. marcescens | − | 3 | 1.9 | 2.5 | 2.3 | 7.1 | 3.1 | 5.6 | 3.5 |
| P. stuartii | − | 2 | 7.7 | 2.8 | 2.3 | 4.4 | 1.6 | 8.6 | 19.7 |
|  |  | 1 | 15.5 | 4 | 4.6 | 17.8 | 6.4 | 17.2 | 28 |
| P. aeruginosa | − | 1 | 15.5 | 2 | 2.3 | 4.4 | 6.4 | 271 | 7 |
|  |  | 1 | 15.5 | 4 | 9.3 | 4.4 | 51.1 | 271 | 443 |
|  |  | 1 | 15.5 | 4 | 18.6 | 35.6 | 25.5 | 271 | >880 |
|  |  | 1 | 15.5 | 4 | 2.3 | 17.8 | 29.6 | 539 | 443 |
|  |  | 19 | 17.2 | 4.5 | 2.2 | 21.4 | 29.4 | 281 | 5.4 |
|  |  | 5 | 23.4 | 12.1 | 2.8 | 20.5 | 29.3 | 539 | 8.4 |
|  |  | 2 | 15.5 | 8 | 6.1 | 17.8 | 32.4 | 271 | 443 |

Chlorhexidine diphosphanilate dihydrate: $C_{34}H_{50}Cl_2N_{12}O_8P_2$, 887.71.
Chlorhexidine digluconate: $C_{34}H_{54}Cl_2O_{14}N_{10}$, 897.80.
Chlorhexidine diacetate: $C_{26}H_{38}Cl_2N_{10}O_4$, 625.56.

The results of Table III clearly indicate that the novel chlorhexidine dinalidixate and diphosphanilic salts of the instant invention are potent and exhibit synergistic effect particularly against P. aeruginosa with the nalidixate salt being the most widely synergistic. The synergistic effect of chlorhexidine dinalidixate is clearly seen by comparison of the results of Table III for *K. pneumoniae, E. cloacae, P. mirabilis, P. morganii, P. rettgeri, P. vulgaris, S. marcescens, P. stuartii* and *P. aeruginosa*. For example, chlorhexidine dinalidixate is seen to have an MIC of 2.9 as against two strains of *K. pneumoniae* and 8.2 against one strain of this organism. The corresponding values for nalidixic acid are 48.7 and 68.9; while those for chlorhexidine digluconate and chlorhexidine diacetate are respectively 70.1 and 35.6 and 51.1 and 51.1.

The novel chlorhexidine dinalidixate of the present invention is seen to display a most impressive synergistic effect as against *P. aeruginosa*. Against 26 strains of this organism, chlorhexidine dinaladixate exhibited an MIC of 50:1; against five strains of such organism, it exhibited an MIC of 43.2; while against one strain of such organism, it exhibited an MIC of 32.9. In contrast thereto, nalidixic acid exhibited against these strains, MIC values, in each case, of more than 539 while chlorhexidine digluconate and chlorhexidine diacetate exhibited, as against the same strains, MIC values of respectively more than 139, more than 139 and 139 and more than 200, 200 and 200.

The synergistic effect of chlorhexidine dinalidixate is also clearly demonstrated from the results of Table IV. Synergisim is seen as against *K. pneumoniae, E. cloacae, P. mirabilis, P. rettgeri, S. marcescens, P. stuartii* and *P. aeruginosa*.

Referring again to Table III, chlorhexidine diphosphanilate of the present invention demonstrates marked synergism against *S. viridans, P. mirabilis, P. vulgaris,* one strain of *P. stuartii* and numerous strains of *P. aeruginosa*.

The results of Table IV demonstrate the asserted synergism of chlorhexidine diphosphanilate as against one strain of *P. rettgeri* and numerous strains of *P. aeruginosa*.

The present invention also contemplates dermatological compositions comprising a novel chlorhexidine salt of the instant invention and a dermatologically acceptable carrier therefor.

Suitable compositions include creams, lotions, suspensions, emulsions, ointments and pastes, and surgical scrubs.

Compositions in which a novel chlorhexidine salt of the present invention is produced in such compositions, in situ, are also within the scope of the invention.

The following formulations are offered to illustrate the compositions of the invention. Although a particular formulation utilizes one of the novel compounds of the invention, it should be readily appreciated that any of the novel compounds or, for that matter, a mixture of such compounds, could be employed in lieu thereof.

Formulations 1 through 3, set forth in Table V which follows, are prepared according to the following general procedure.

In a suitably sized premix container, the stearyl alcohol is dissolved in the Petrolatum with the aid of heat and gentle stirring. The temperature is then adjusted to about 62° to 68° C.

The propylene glycol and about 99% of the purified water are combined in a suitably sized, preferably jacketed, main mix vessel and stirred until a homogeneous solution is obtained. The resultant solution is heated to 62° to 68° C. then subjected to high speed mixing (preferably utilizing a suitable propeller mixture such as the Lightning model ARL air mixer or similar type apparatus). The Carbomer is then slowly added thereto. High speed mixing is continued until the Carbomer is completely dispersed (approximately one hour). The sodium lauryl sulfate, sorbic acid and the amphoteric-9 are then added, while mixing slowly, and the resultant mixture is mixed slowly until it is homogeneous.

In a suitably sized container, the remainder of the water (about 1%) is heated to about 40° to 45° C. then the dried sodium phosphate is added thereto under rapid stirring. The stirring is continued until a clear solution results. The clear sodium phosphate solution is then added to the mixture in the main mix vessel while mixing slowly. Mixing is continued until a smooth semi-gel is formed. While mixing slowly, heating is initiated. The temperature is adjusted to about 62° to 68° C.

The petrolatum and stearyl alcohol, constituting the oil phase, are then slowly added to the main mix vessel containing the ingredients constituting the aqueous phase. This addition is made while mixing the aqueous phase at high speed. Mixing is continued for a period of about 5 to 10 minutes then cooling is initiated (preferably by circulation of cold water in the outer jacket of the main mix vessel). During this cooling operation, the mixture is subjected to slow speed agitation (preferably using a side scraping sweep agitator of the Groen type or the like). The mixture is cooled to a temperature of about 25° to 30° C. whereby a finished base is produced.

A small amount of the finished base (an amount sufficient to produce a workable consistency; about 5% in the case of Formulation 1; about 10% in the case of Formulation 2 and about 15% in the case of Formulation 3) is added to a suitably sized container. The novel chlorhexidine salt of the present invention is added thereto and mixed therewith (with the aid of a spatula or suitable mixer) until it is uniformly dispersed in the finished lotion base. The dispersion is passed through a roller mill (preferably of the Asra type or the like) at an appropriate setting to produce a fine non-gritty particle size. This procedure is repeated if necessary whereby a milled concentrate is obtained.

The milled concentrate is then added to the remaining finished base and mixed therewith at slow speed (preferably using a sweep agitator) for one hour or until the uniform dispersion is formed.

TABLE V

| Formulation | Percentage (by weight) No. | | |
|---|---|---|---|
| | 1 | 2 | 3 |
| Chlorhexidine dinalidixate | 1.00 | 3.00 | 5.00 |
| Chlorhexidine diphosphanilate | — | — | — |
| Propylene glycol, USP | 12.00 | 12.00 | 12.00 |
| Petrolatum, USP | 22.50 | 22.50 | 22.50 |
| Stearyl alcohol, USP | 15.00 | 15.00 | 15.00 |
| Amphoteric-9 | 0.66 | 0.66 | 0.66 |
| Carbomer-940 | 0.50 | 0.50 | 0.50 |
| Sodium lauryl sulfate, USP | 0.10 | 0.10 | 0.10 |
| Sorbic acid NF | 0.10 | 0.10 | 0.10 |
| Dried sodium phosphate | 0.25 | 0.25 | 0.25 |
| Purified water qs to | 100.00 | 100.00 | 100.00 |

Formulations 4, 5 and 6, set forth in Table VI which follows, are prepared according to the following general procedure:

The Peg-8 and the lactic acid are added to a, preferably stainless steel, premix container of suitable size and mixed slowly until a homogeneous solution is obtained.

The petrolatum, mineral oil, lanolin oil, cetyl alcohol, hydrogenated polyisobutene, Peg-40 stearate, benzyl alcohol and sodium lauryl sulfate are added to a main mix vessel which is preferably of stainless steel and steam jacketed (e.g. Groen Model TDC/2-20 or the like). The mixture is agitated slowly (preferably using a Lightning air mixer or a similar type mixture equipped with a propeller type blade) and heated. Mixing and heating are continued until all solids are melted. The temperature is adjusted to about 65° to 70° C. Mixing is continued for about 10 minutes then heating and agitation are discontinued. The mixture is then cooled (preferably by introduction of cold water into the outer jacket) and slow speed mixing is initiated (preferably with a side scraping sweep agitator). The mixture is permitted to cool to about 40° to 45° C. during which time continuous mixing is maintained.

The solution of lactic acid and Peg-8 is then added to the ingredients contained in the main mix vessel, said ingredients constituting the oil phase. The addition is carried out slowly and with constant mixing. Mixing and cooling are continued until a temperature of about 25° to 30° C. is attained whereby a finished base is produced.

A small amount of the finished base (viz. an amount sufficient to produce a workable consistency; approximately 5% in the case of Formulation 4, approximately 10% in the case of Formulation 5 and approximately 15% in the case of Formulation 6) is added to a suitably sized mixing container (for example a Hobart Model A-200D or the like) and the chlorhexidine diphosphanilate is added thereto. The combination of the chlorhexidine diphosphanilate and finished base is mixed slowly until a fairly uniform dispersion of the salt results. The dispersion is passed through a roller mill (preferably of the Asra type or the like) at an appropriate setting to produce a fine non-gritty particle size whereby a milled concentrate is obtained.

The milled concentrate is added to the finished base and mixed therewith at slow speed (preferably employing a side scraping sweep agitator, for example of the Groen type or the like) for about one hour or until a homogeneous dispersion is obtained.

TABLE VI

| Formulation | Percent (by weight) No. | | |
|---|---|---|---|
| | 4 | 5 | 6 |
| Chlorhexidine diphosphanilate | 1.000 | 3.000 | 5.000 |
| Mineral Oil USP | 10.000 | 10.000 | 10.000 |
| Peg-8 | 8.000 | 8.000 | 8.000 |
| Lanolin oil | 4.000 | 4.000 | 4.000 |
| Cetyl alcohol | 3.000 | 3.000 | 3.000 |
| Hydrogenated polyisobutene | 3.000 | 3.000 | 3.000 |
| Peg-40 stearate | 2.000 | 2.000 | 2.000 |
| Benzyl alcohol | 0.500 | 0.500 | 0.500 |
| Sodium lauryl sulfate USP | 0.100 | 0.100 | 0.100 |
| Lactic acid (88%) | 0.002 | 0.002 | 0.002 |
| Petrolatum USP qs to | 100.000 | 100.000 | 100.000 |

Formulations 7 and 8, set forth in Table VII which follows, are produced according to the following general procedure:

The glyceryl oleate/propylene glycol, Peg-7-hydrogenated castor oil, sorbitan oleate, oleoyl hydrogenated animal protein, Arlacel 481, light mineral oil, hydrogenated polyisobutene, lanolin alcohol/mineral Oil, caprylic/capric triglycerides, propyl paraben and beeswax are added to a, preferably stainless steel and jacketed, premix container of suitable size. The mixture is subjected to heating and slow mixing (preferably with a Lightning Model ARL air mixer with propeller type agitator or similar apparatus). The temperature is adjusted to about 75° to 85° C. whereby an oil phase is produced.

The water, lactic acid, propylene glycol and dried sodium phosphate are added to a main mixing vessel which is preferably of stainless steel and jacketed (for example the Groen Model TDC/2-20 or similar apparatus). This addition is made while heating and mixing at moderate speed (preferably employing a Lightnin Model ARL air mixer or the like). Mixing is continued until a clear solution is formed, then the sorbitol, methyl paraben and the titanium dioxide are added. Mixing and heating are continued until a homogeneous mixture is produced. The temperature is adjusted to about 75° to 85° C. whereby a water phase is produced.

When the water phase and the oil phase are at a proper temperature, the oil phase is added slowly to the water phase where mixing constantly at moderate speed (preferably employing a Lightnin Model ARL air mixer of similiar apparatus) whereby an emulsion is produced. The magnesium stearate is added to the emulsion and mixed therewith for about 20 minutes at a temperature of about 75° to 85° C. The heating is then discontinued (preferably by introduction of cold water into the outer jacket of the main mixing vessel). Slow speed mixing is initiated, preferably using a side scraping sweep agitator (such as the Groen Model TDC/2-20 style agitator or similar apparatus). Mixing and cooling are permitted to continue until the temperature reaches about 25° to 30° C. whereby a finished base is produced.

A small amount of the finished base (viz. an amount sufficient to produce a workable consistency; about 10% in the case of Formulation 7 and about 15% in the case of Formulation 8) is added to a suitably sized container. The novel chlorhexidine salt of the present invention is then added thereto and mixed therewith using a spatula or other suitable mixer until a fairly uniform dispersion of the salt in the ointment base results. This dispersion is passed one or more times through a roller mill of suitable capacity (preferably of the Asra type or the like) at an appropriate mill setting to produce a fine non-gritty particle size whereby a milled concentrate is produced.

The milled concentrate is added to the remaining finished base and mixed therewith (preferably using a Groen sweep agitator or similar equipment) at slow speed for about one hour or until a homogeneous dispersion is formed.

TABLE VII

| Formulation | Percent (by weight) No. | |
|---|---|---|
| | 7 | 8 |
| Chlorhexidine dinalidixate | 3.00 | — |
| Chlorhexidine diphosphanilate | — | 5.00 |
| Propylene glycol | 12.00 | 12.00 |
| Light mineral oil USP | 10.84 | 10.84 |
| Hydrogenated polyisobutene | 10.00 | 10.00 |
| Caprylic/capric triglycerides | 10.00 | 10.00 |
| Beeswax | 10.00 | 10.00 |
| Peg-7-Hydrogenated castor oil | 8.00 | 8.00 |
| Lanolin alcohol/mineral oil | 6.00 | 6.00 |
| Arlacel 481 | 4.00 | 4.00 |
| Sorbitol | 3.00 | 3.00 |
| Glyceryl oleate/propylene glycol | 2.00 | 2.00 |
| Sorbitan oleate | 2.00 | 2.00 |
| Oleoyl hydrogenated animal protein | 2.00 | 2.00 |
| Magnesium stearate | 2.00 | 2.00 |
| Titanium dioxide | 1.00 | 1.00 |
| Methyl paraben | 0.25 | 0.25 |
| Propyl paraben | 0.20 | 0.20 |

TABLE VII-continued

| Formulation | Percent (by weight) No. 7 | No. 8 |
|---|---|---|
| Dried sodium phosphate | 0.11 | 0.11 |
| Lactic acid (88%) | 0.10 | 0.10 |
| Purified water qs to | 100.00 | 100.00 |

The novel chlorhexidine salts of the present invention represent an unusual approach to the synthesis of superior antimicrobials. The data of Tables I through IV clearly demonstrate that these chlorhexidine salts possess unexpected and medically useful antibacterial properties.

Chlorhexidine is a known antimicrobial agent. Attempts have been made in the prior art to synthesize the "best" salts of chlorhexidine for various applications. However, prior art attempts in this regard have utilized an entirely different approach than the employed herein. In the prior art approach, chlorhexidine salts are made with materials which do not of themselves possess any significant general antimicrobial activity as compared to chlorhexidine. As would be expected, some prior art chlorhexidine salts have better activity or more desirable physical properties than other of such salts. However, any improved activity is merely a fortuitous result of such synthetic approach. The approach used in the present invention viz. reacting two antimicrobial compounds to produce a new antimicrobial compound which is formed solely the two "parent" antimicrobials is quite distinct from the prior art approach of making a simple salt of an antimicrobial or mixing two antimicrobial agents to produce a mixture having advantageous properties. For most combinations of antimicrobials, the formation of a useful antimicrobial compound from two known antimicrobials is not a feasible or rational means of seeking improved antimicrobial properties.

The data of Table I-IV show that the novel chlorhexidine salts disclosed herein are surprisingly and unexpectedly superior to like concentrations of their components or like concentrations of simple mixtures of their components. This superiority is seen in that:

(a) The test data of Tables I-IV show that the chlorhexidine salts of the present invention, when tested against the specified bacteria, are free from undesirable antagonistic properties of a simple mixture of the parent compounds;

(b) The chlorhexidine nalidixate and phosphanilate salts unexpectedly exhibit a broader spectrum of antibacterial activity than other chlorhexidine derivatives;

(c) Chlorhexidine nalidixate and phosphanilate exhibit substantially better activity against the majority of strains of *Pseudomonas aeruginosa*, an organism commonly encountered in burn infections. This is an extremely important and novel activity. There has been considerable interest in the skin degerming activity of chlorhexidine derivatives and their ability to prevent burn infections; however, prior art chlorhexidine compounds uniformly exhibit inadequate activity against many *Pseudomonas aeruginosa* strains. The surprising activity of chlorhexidine nalidixate and phosphanilate against the majority of strains of *Pseudomonas aeruginosa* tested is extremely important to the medical profession and constitutes a potentially significant advance in the treatment and prevention of burn infections.

The following analysis is offered in substantiation of points (a), (b) and (c) above. Chlorhexidine nalidixate was employed since the test data of Tables I-IV include the results of testing a 1:1 mixture of chlorhexidine digluconate and nalidixic acid.

Various methods have been employed to support a claim of synergism. The most desirable involve calculation of a numerical value for synergy to facilitate comparisons. One such prior art recognized method is that of Kull et al, Applied Microbiology 9,538-541, 1961. This method of calculation has been used in support of several (possibly many) United States patents, for example, U.S. Pat. No. 3,989,585 of Swered et al.

The following formula is used:

$$\frac{Q_A}{Q_a} + \frac{Q_B}{Q_b} = \text{Synergism Index}$$

| Value of Synergism Index | Indicates |
|---|---|
| >1 | Antagonism |
| ≈1 | Additivity |
| <1 | Synergism | where $Q_A$, $Q_B$ = quantities of compounds A or B, respectively, in the mixture at the minimum inhibitory concentration $Q_a$, $Q_b$ = quantities of compounds A or B, respectively, acting alone to produce an end point.

The data of Table II were employed in calculating a Synergism Index for chlorhexidine digluconate and for nalidixic acid, as against various organisms. The method of Kull et al was utilized and the results are shown in the following Table VIII.

TABLE VIII

Synergism Index for Chlorhexidine Digluconate and Nalidixic Acid from Data of Table II

| Organism | $\frac{Q_A}{Q_a}$ | $\frac{Q_B}{Q_b}$ | $\frac{Q_A}{Q_a} + \frac{Q_B}{Q_b}$ = Synergism Index |
|---|---|---|---|
| S. aureus | 2.40 | .02 | 2.42 (Antagonistic) |
| S. pneumoniae | 4.90 | <.40 | >4.90 (Antagonistic) |
| S. pyogenes | 2.48 | <.06 | >2.48 (Antagonistic) |
| S. viridans | 1.97 | <.25 | >1.97 (Antagonistic) |
| Streptococcus (B-hemolytic) | 5.71 | <.06 | >5.71 (Antagonistic) |
| S. faecalis | 2.83 | <.05 | >2.83 (Antagonistic) |
| E. coli | .79 | .25 | 1.04 (Additive) |
| K. pneumoniae | .18 | .25 | .43 (Synergistic) |
|  | .25 | .25 | .50 (Synergistic) |
| E. cloacae | .13 | .25 | .38 (Synergistic) |
|  | .25 | .35 | .60 (Synergistic) |
| P. mirabilis | .75 | .25 | 1.00 (Additive) |
| P. rettgeri | .03 | 1.00 | 1.03 (Additive) |
|  | .16 | 1.00 | 1.16 (Additive) |
| P. vulgaris | 1.00 | 4.00 | 5.00 (Antagonistic) |
| S. marcescens | .20 | .96 | 1.16 (Additive) |
| P. stuartii | .25 | 1.00 | 1.25 (Additive) |
|  | .25 | 1.00 | 1.25 (Additive) |
| P. aeruginosa | 1.00 | .06 | 1.06 (Additive) |
|  | 1.00 | .06 | 1.06 (Additive) |
|  | .13 | .06 | .19 (Synergistic) |
|  | .25 | <.03 | >.25 (Synergistic) |
|  | .23 | .07 | .30 (Synergistic) |
|  | .33 | <.05 | >.33 (Synergistic) |
|  | .25 | .06 | .31 (Synergistic) |

Compound A = Chlorhexidine Digluconate
Compound B = Nalidixic Acid

It can be seen from the results of Table VIII that for some organisms, particularly gram-positive cocci, the actions of nalidixic acid and chlorhexidine digluconate are strongly antagonistic, In other words, it takes a higher concentration of the mixture of nalidixic acid and chlorhexidine digluconate to inhibit the test organism than would be expected from the amount of each pure compound required to inhibit the same organism.

It is further evident from the data of Table VIII that cases of additivity also exist and for some organisms (particularly *Pseudomonas aeruginosa*) the actions of nalidixic acid and chlorhexidine digluconate are synergistic.

For comparative purposes, the Minimum Inhibitory Concentration (MIC) of chlorhexidine nalidixate is compared to the MIC of chlorhexidine digluconate and to the MIC of a 1:1 mixture of chlorhexidine digluconate and nalidixic acid in the following Table IX. Table IX also sets forth the Synergism Index for the 1:1 mixture of chlorhexidine diguconate and nalidixic acid as calculated and shown in Table VIII. To facilitate such comparison the MIC of the 1:1 mixture of chlorhexidine digluconate and nalidixic acid was corrected to exclude the weight portion that is "digluconate" (about 22%). The results are set forth in the column of Table IX labeled "Corrected MIC 1/1 Mixture". This weight correction would not be necessary if it were possible to test pure chlorhexidine; however, chlorhexidine base is unstable and any MIC data generated with it would be unreliable.

ate and nalidixic acid with the lower MIC's of the chlorhexidine nalidixate salts.

The data of Table IX further demonstrate that in those cases where the mixture of chlorhexidine digluconate and nalidixic acid have a Synergism Index indicative of a synergistic result, the synergistic properties are preserved by formation of the chlorhexidine nalidixate salt.

It is surprising and unexpected that formation of the chlorhexidine nalidixate salt eliminates the antagonism obtained with a mixture of chlorhexidine digluconate and nalidixic acid.

The data of Table IX show that chlorhexidine nalidixate has novel activity against *Pseudomonas aeruginosa*. MIC comparisons demonstrate that it is significantly better than chlorhexidine digluconate, which is available commercially and heretofore generally recognized as the best available chlorhexidine derivative.

In summary, the data of Tables VIII and IX show that chlorhexidine nalidixate surprisingly and unexpectedly eliminates the undesirable antagonistic properties of a comparable mixture of its components (viz. a 1:1 mixture of chlorhexidine digluconate and nalidixic acid) while preserving desirable synergistic properties and

TABLE IX

Comparison Table (MIC's in μg/ml)

| Organism | Synergism Index Result for 1/1 Mixture | MIC of 1/1 Chlorhexidine Digluconate and Nalidixic Acid | Corrected MIC 1/1 Mixture | MIC Chlorhexidine Digluconate | MIC Chlorhexidine Nalidixate |
|---|---|---|---|---|---|
| S. aureus | Antagonistic | 1.2 | .94 | .25 | .21 |
| S. pneumoniae | Antagonistic | 99.5 | 77.9 | 10.1 | 12.7 |
| S. pyogenes | Antagonistic | 16 | 12.5 | 3.2 | 4 |
| S. viridans | Antagonistic | 63 | 49.3 | 16 | 16 |
| Streptococcus | Antagonistic | 16 | 12.5 | 1.4 | 4 |
| S. faecalis | Antagonistic | 11.3 | 8.8 | 2 | 8 |
| E. coli | Additive | 1 | .78 | .63 | .63 |
| K. pneumoniae | Synergistic | 1.4 | 1.1 | 4 | 1 |
| | Synergistic | 2 | 1.6 | 4 | 1 |
| E. cloacae | Synergistic | 1 | .78 | 4 | 1 |
| | Additive | 1.4 | 1.1 | 2.8 | 1 |
| P. mirabilis | Additive | 6.4 | 5.0 | 12.7 | 4 |
| P. rettgeri | Additive | 0.5 | .39 | 8 | .5 |
| | Additive | 5 | 3.9 | 16 | 4 |
| P. vulgaris | Antagonistic | 4 | 3.1 | 2 | 1 |
| S. marcescens | Additive | 2.5 | 2.0 | 6.4 | 2.5 |
| P. stuartii | Additive | 4 | 3.1 | 4 | 2.8 |
| | Additive | 8 | 6.3 | 16 | 4 |
| P. aeruginosa | Additive | 8 | 6.3 | 4 | 2 |
| | Additive | 8 | 6.3 | 4 | 4 |
| | Synergistic | 8 | 6.3 | 32 | 4 |
| | Synergistic | 8 | 6.3 | 16 | 4 |
| | Synergistic | 8.9 | 7.0 | 19.2 | 4.5 |
| | Synergistic | 12.1 | 9.5 | 18.4 | 8 |
| | Synergistic | 8 | 6.3 | 16 | 8 |

Note
Underlined values are for the most synergistic and most antagonistic examples.

The data of Table IX clearly show that in those cases where the chlorhexidine digluconate/nalidixid acid mixture was determined to have a Synergism Index indicative of antagonistic properties, the antagonism was eliminated by the synthesis of the chlorhexidine nalidixate salt. This is evident from a comparison of the higher MIC's of the mixture of chlorhexidine digluconate and nalidixic acid with the lower MIC's of the chlorhexidine nalidixate salts.

providing a unique and useful broad spectrum of activity.

MIC tests were carried out on a 1:1 mixture of chlorhexidine digluconate and phosphanilic acid. These MIC tests were conducted in the usual manner on solidified Mueller-Hinton medium. The method employed corresponds to that employed in generating the data of Tables I-IV.

The following Table X sets forth the test results.

TABLE X

| Organism | # of Strains | Chlorhexidine Digluconate | Chlorhexidine Digluconate Phosphan. 1/1 mixture Straight Geometric mean values where applicable | Chlorhexidine Diphosphanilate Dihydrate | Phosphanilic Acid |
|---|---|---|---|---|---|
| S. aureus | 1 | 1 | 1 | .5 | 32 |
|  | 2 | .71 | 1 | .35 | >125 |
|  | 3 | .63 | 1 | .79 | >125 |
| S. pneumoniae | 3 | 10.1 | 20.2 | 10.1 | >125 |
| S. pyogenes | 4 | 2.8 | 2.8 | 1.7 | >125 |
| S. viridens | 1 | 16 | 32 | 16 | >125 |
| β-hemolytic Streptococcus | 2 | 4 | 8 | 4 | >125 |
| S. faecalis | 2 | 2 | 2.8 | 2 | >125 |
| E. coli | 3 | 2 | 4 | 1.3 | 99.5 |
| K. pneumoniae | 1 | 32 | 32 | 8 | 6.3 |
| E. cloacae | 1 | 4 | 32 | 4 | >125 |
| P. mirabilis | 2 | 63 | 11.3 | 4 | 5.7 |
| P. morgani | 1 | 1 | 4 | 2 | 8 |
|  | 1 | 8 | 32 | 8 | 125 |
| P. rettgeri | 3 | 25.3 | 8 | 8 | 1.6 |
| P. vulgaris | 1 | 8 | 16 | 4 | 4 |
| S. marcescens | 3 | 12.7 | 6.4 | 6.4 | 2 |
| P. stuartii | 3 | 10.1 | 6.4 | 5 | 2.5 |
| P. aeruginosa | 15 | 52.6 | 1.1 | 2.1 | .69 |
|  | 10 | 48.1 | 4.6 | 3.3 | 1.7 |
|  | 1 | 8 | 8 | 8 | 32 |
|  | 5 | 82.9 | 8 | 8 | <63 |

The method of Kull et al, previously referred to, was employed in calculating the Synergism Indices of the following Table XI.

TABLE XI

Calculation of Synergism Index for Chlorhexidine Digluconate and Phosphanilic Acid Compound A = Chlorhexidine digluconate
Compound B = Phosphanilic acid

| Organism | $\frac{Q_A}{Q_a}$ | $\frac{Q_B}{Q_b}$ | $\frac{Q_A}{Q_a} + \frac{Q_B}{Q_b} =$ Synergism Index |
|---|---|---|---|
| S. aureus | .50 | .02 | .52 (Synergistic) |
|  | .70 | .004 | .70 (Synergistic) |
|  | .79 | <.004 | >.79 (Synergistic) |
| S. pneumoniae | 1.00 | <.08 | >1.08 (Additive) |
| S. pyogenes | .50 | <.01 | >.50 (Synergistic) |
| S. viridans | 1.00 | <.13 | >1.13 (Additive) |
| B-hemolytic Streptococcus | 1.00 | <.03 | >1.03 (Additive) |
| S. faecalis | .70 | <.01 | >.71 (Synergistic) |
| E. coli | 1.00 | .02 | 1.02 (Additive) |
| K. pneumoniae | .50 | .25 | .75 (Synergistic) |
| E. cloacae | 4.00 | <.13 | >4.13 (Antagonistic) |
| P. mirabilis | .09 | .99 | 1.08 (Additive) |
| P. morgani | 2.00 | .25 | 2.25 (Antagonistic) |
|  | 2.00 | .13 | 2.13 (Antagonistic) |
| P. rettgeri | .16 | 2.50 | 2.66 (Antagonistic) |
| P. vulgaris | 1.00 | 2.00 | 3.00 (Antagonistic) |
| S. marcescens | .25 | 1.60 | 1.85 (Antagonistic) |
| P. stuartii | .32 | 1.28 | 1.60 (Antagonistic) |
| P. aeruginosa | .01 | .80 | .81 (Synergistic) |
|  | .05 | 1.35 | 1.40 (Antagonistic) |
|  | .50 | .13 | .63 (Synergistic) |
|  | .05 | ? | — |

The data of Table XI show that mixtures of chlorhexidine digluconate and phosphanilic acid exhibit varying properties against the different test organisms and that the pattern of synergism/antagonism differs from that of chlorhexidine digluconate/nalidixic acid mixtures. The chlorhexidine digluconate/phosphanilic acid mixture shows synergism or additivity against gram-positive cocci, and wide variation between antagonism and synergism against gram-negative bacilli. This is almost completely opposite to the synergism pattern shown by the mixture of chlorhexidine digluconate and nalidixic acid. For most strains of *Pseudomonas aeruginosa,* the mixture of chlorhexidine digluconate and phosphanilic acid is synergistic or weakly antagonistic.

In the following Table XII, MIC values for the compounds are compared to the Synergism Indices shown in Table XI. The novel and unexpected properties of the chlorhexidine phosphanilate salt are apparent from the data of Table XII. To facilitate comparison, the MIC of the mixture in Table XII has been corrected to eliminate the weight portion which is "digluconate", about 22%. This was done because pure chlorhexidine base is unstable and cannot be tested for direct comparison.

TABLE XII

Comparison Table for Novel Properties of Chlorhexidine Phosphanilate (MIC's in μg/ml)

| Organism | Synergism Index Result for 1/1 Mixture | MIC of 1/1 Chlor. digluconate & Phosphanilic acid | Corrected MIC 1/1 Mixture | MIC Chlorhexidine Digluconate | MIC Chlorhexidine Phosphanilate |
|---|---|---|---|---|---|
| S. aureus | Synergistic | 1 | .78 | 1 | .5 |
|  | Synergistic | 1 | .78 | .71 | .35 |
|  | Synergistic | 1 | .78 | .63 | .79 |

TABLE XII-continued

Comparison Table for Novel Properties
of Chlorhexidine Phosphanilate
(MIC's in μg/ml)

| Organism | Synergism Index Result for 1/1 Mixture | MIC of 1/1 Chlor. digluconate & Phosphanilic acid | Corrected MIC 1/1 Mixture | MIC Chlorhexidine Digluconate | MIC Chlorhexidine Phosphanilate |
|---|---|---|---|---|---|
| S. pneumoniae | Additive | 20.2 | 15.8 | 10.1 | 10.1 |
| S. pyogenes | Synergistic | 2.8 | 2.2 | 2.8 | 1.7 |
| S. viridans | Additive | 32 | 25.0 | 16 | 16 |
| B-hemolytic Streptococcus | Additive | 8 | 6.3 | 4 | 4 |
| S. Faecalis | Synergistic | 2.8 | 2.2 | 2 | 2 |
| E. coli | Additive | 4 | 3.1 | 2 | 1.3 |
| K. pneumoniae | Synergistic | 32 | 25.0 | 32 | 8 |
| E. cloacae | Antagonistic | _32_ | _25.0_ | _4_ | _4_ |
| P. mirabilis | Additive | 11.3 | 8.8 | 63 | 4 |
| P. morgani | Antagonistic | 4 | 3.1 | 1 | 2 |
|  | Antagonistic | 32 | 25.0 | 8 | 8 |
| P. rettgeri | Antagonistic | 8 | 6.3 | 25.3 | 8 |
| P. vulgaris | Antagonistic | _16_ | _12.5_ | _8_ | _4_ |
| S. marcescens | Antagonistic | 6.4 | 5.0 | 12.7 | 6.4 |
| P. stuartii | Antagonistic | 6.4 | 5.0 | 10.1 | 5 |
| P. aeruginosa | Synergistic | 1.1 | .86 | 52.6 | 2.1 |
|  | Antagonistic | 4.6 | 3.6 | 48.1 | 3.3 |
|  | Synergistic | 8 | 6.3 | 8 | 8 |
|  | — | 8 | 6.3 | 82.9 | 8 |

NOTE:
Underlined values are for the most synergistic and most antagonistic examples.

The data of Table XII clearly show that in cases where the mixture of chlorhexidine digluconate and phosphanilic acid had its strongest antagonistic properties (see the two cases underlined in Table XII), the antagonism was eliminated by synthesis of the chlorhexidine phosphanilate salt. This is seen from a comparison of the higher MIC's of the mixture with the lower MIC's of the chlorhexidine phosphanilate salt.

The data of Table XII further show that in cases where the mixture of chlorhexidine digluconate and phosphanilic acid was synergistic, the synergistic properties were preserved by the formation of the chlorhexidine phosphanilate salt. What is more important for general antibacterial usage is the fact that the MIC's for chlorhexidine phosphanilate are substantially better than the MIC's of the mixture of chlorhexidine digluconate and phosphanilic acid and the MIC's of chlorhexidine digluconate which is generally recognized as the best available chlorhexidine derivative.

It is important to note that the activity of chlorhexidine phosphanilate against *Pseudomonas aeruginosa* is far superior to that of chlorhexidine digluconate in 30 of the 31 tested strains, and is equal for the remaining strain. It is evident that chlorhexidine phosphanilate is an important antibacterial agent having potential use in the treatment of burns, where pseudomonal infections are commonplace.

The data of Table II demonstrate the superior activity of chlorhexidine phosphanilate against *Pseudomonas aeruginosa* and gram-positive Staphylococcus and Streptococcus species. Phosphanilic acid gives MIC's >125 μg/ml while chlorhexidine digluconate and chlorhexidine phosphanilate give MIC's from 0.25–16 μg/ml. From this data it may be concluded that, for these organisms, chlorhexidine phosphanilate is far superior to phosphanilic acid and as good as the best commercial material, chlorhexidine digluconate.

Referring now to the activity of chlorhexidine phosphanilate against gram-negative rods other than Pseudomonas: Phosphanilic acid MIC's are from 0.5->125 μg/ml while chlorhexidine digluconates MIC's are from 0.63–16 μg/ml and chlorhexidine phosphanilates MIC's are from 0.63–6.4 μg/ml. These data show that chlorhexidine phosphanilate is far superior to phosphanilic acid and better than chlorhexidine digluconate.

Referring further to the activity of chlorhexidine phosphanilate against *Pseudomonas aeruginosa* illustrated in Table II: In screening antimicrobials for useful activity in media relatively free of antagonists (such as used in the tests employed to generate the results of Table II), 16 μg/ml is the generally accepted cut-off point for useful activity. It is evident from the data that in all Pseudomonas cases, chlorhexidine phosphanilate meets this criterion while chlorhexidine digluconate is marginal or a failure against 93% of the tested strains. Phosphanilic acid fails by a significant (fourfold) margin against 17% of the tested strains. More importantly, chlorhexidine phosphanilate not only meets the cut-off criterion against 100% of the tested strains, it surpasses the cut-off by a significant (fourfold or better) margin as against 87% of the tested *Pseudomonas aeruginosa* strains.

The superior activity of chlorhexidine phosphanilate is also seen in Table III, particularly with reference to activity against gram-positive Staphylococcus and Streptococcus species. Phosphanilic acid gives MIC's >880 millimoles/ml while chlorhexidine digluconate and chlorhexidine phosphanilate give MIC's of from 0.3 to 17.8 or 18.6 millimoles/ml. From these data, one can conclude that, for these organisms, chlorhexidine phosphanilate is far superior to phosphanilic acid and as good as the best commercial material, chlorhexidine digluconate.

Turning now to the activity of chlorhexidine phosphanilate against gram-negative rods other than Pseudomonas (this includes all of the organisms of Table III except for Pseudomonas and the gram-positive cocci [viz. Staphylococcus and Streptococcus] species). Phosphanilic acid exhibits MIC's of from 3.5 to >880 millimoles/ml while chlorhexidine digluconate exhibits MIC's of from 0.7 to 17.8 millimoles/ml. In contrast thereto, chlorhexidine phosphanilate exhibits MIC's of from 0.7 to 7.4 millimoles/ml against the aforementioned gram-negative rods. It is clear from these data that chlorhexidine phosphanilate is far superior to phosphanilic acid and slightly better than chlorhexidine digluconate.

Table III lends further support to the novel activity of chlorhexidine phosphanilate against *Pseuodomonas aeruginosa*. As is seen in Table III, phosphanilic acid MIC's as against this organism range from 5.4 to >880 millimoles/ml; chlorhexidine digluconate MIC's as against this organism range from 4.4 to 35.6 millimoles/ml; while chlorhexidine phosphanilate MIC's as against this organism range from 2.2 to 18.6 millimoles/ml. These data make it abundantly clear that as against *Pseudomonas aeruginosa*, chlorhexidine phosphanilate is significantly superior on a mole basis to phosphanilic acid and to chlorhexidine digluconate.

The results of Tables II and III clearly demonstrate the useful and novel properties of chlorhexidine phosphanilate irrespective of whether the data is analyzed on a weight or molar basis.

Data analyzed previously in Tables VIII and XI indicate that 1-1 mixtures of chlorhexidine digluconate and nalidixic or phosphanilic acid have a synergistic effect against certain microorganisms. To elucidate the scope of this synergism, further experiments were conducted with additional compounds and at varying concentration ratios. The experiments tested chlorhexidine HCl, chlorhexidine digluconate, and chlorhexidine diacetate in combination with phosphanilic acid or nalidixic acid or the sodium or potassium salts of these acids. Mixtures were tested at weight % ratios of 5/95, 25/75, 50/50, 75/25 and 95/5. The compounds in the mixtures were also tested individually. Tests were conducted on solidified Mueller-Hinton medium in a manner similar to previous tests except that the medium was solidified with Noble Agar rather than Ion Agar used previously. The minimum inhibitory concentrations (MIC's) obtained are reported in Tables XIII through XVIII. They are similar to MIC's reported in previous Tables but reflect some differences attributable to the use of different strains, slightly different test conditions, and more intensive replication.

For each mixtures MIC value in Tables XIII through XVIII, a corresponding synergism index value can be calculated according to the method of Kull et al described previously. For example, in Table XIII, the synergism index of 50/50 mixture of chlorhexidine digluconate and nalidixic acid against 14 strains of *Pseudomonas aeruginosa* can be calculated according to the Kull et al formula as:

$$\frac{Q_A}{Q_a} + \frac{Q_B}{Q_b} = \frac{.5(8.4)}{27.6} + \frac{.5(8.4)}{250} = 0.17$$

When all the individual synergism indices corresponding to the mixture MIC's have been calculated, they can be averaged to produce mean synergism indices for each mixture ratio against all test organisms. This is a conservative method of analysis because (1) each mean synergism index represents the overall results of at least duplicate tests against (using Table XIII as an example) 82 bacterial strains and (2) the method of Kull et al sets no theoretical upper limit on index value but restricts values indicating synergism to between zero and 1.0. Therefore, one high index value indicating antagonism can outweigh several low index values indicating synergism, when an average is calculated. The mean synergism indices are displayed in Tables XIX and XX. Mixtures which display a consistent pattern of favorable synergism indices (<1.0) at different concentrations can be considered generally advantageous combinations for antibacterial applications. For example, the combinations of chlorhexidine digluconate with nalidixic acid or its sodium or potassium salts are synergistic at ratios from about 95/5 to about 5/95. Many combinations are synergistic only in narrower ranges. For example, chlorhexidine digluconate potassium phosphanilate is synergistic at ratios from about 75/25 to about 25/75; chlorhexidine digluconate/phosphanilic acid from about 95/5 to about 25/75; chlorhexidine hydrochloride/phosphanilic acid from about 95/5 to about 50/50; chlorhexidine diacetate/nalidixic acid from about 50/50 to about 5/95; and chlorhexidine hydrochloride/potassium nalidixate from about 75/25 to about 5/95. Some mixtures lack general antibacterial synergism. Those tested which fit this category are chlorhexidine diacetate/sodium nalidixate, chlorhexidine diacetate/potassium nalidixate, chlorhexidine digluconate/sodium phosphanilate, chlorhexidine diacetate/phosphanilic acid, chlorhexidine diacetate/sodium phosphanilate, chlorhexidine diacetate/potassium phosphanilate and chlorhexidine hydrochloride/potassium phosphanilate. Mixtures showing only limited general antibacterial value or yielding results difficult to interpre include chlorhexidine hydrochloride/nalidixic acid, chlorhexidine hydrochloride/sodium nalidixate, and chlorhexidine hydrochloride/sodium phosphanilate.

It should be understood that combinations or mixture ratios which lack general antibacterial synergism may nonetheless have synergistic activity against individual species of microorganisms or under conditions different from those of our tests. For limited uses, such combinations or mixture ratios would be advantageous.

It should be noted that dermatological compositions of the synergistic mixtures disclosed herein may be readily prepared by adapting, if need be, the methods and the formulations disclosed herein for the novel dinalidixate and diphosphanilate salts of chlorhexidine of the invention.

TABLE XIII

Antibacterial Activity of Chlorhexidine Digluconate in Combination with Nalidixic Acid (NA) or its Na+ and K+ Salts

| Drug Combinations | | Organism | No. of Strains | MIC (μg/ml)* Chlorhexidine:Nalidixate (%:%) | | | | | | |
|---|---|---|---|---|---|---|---|---|---|---|
| | | | | 100:0 | 95:5 | 75:25 | 50:50 | 25:75 | 5:95 | 0:100 |
| Chlorhexidine | :NA | P. aeruginosa | 14 | 27.6 | 11 | 11 | 8.4 | 14.1 | 60 | ≧250 |
| Digluconate | :Na+ | | 11 | 27.3 | 15 | 13.7 | 6.2 | 16 | 61.1 | ≧228 |
| | :K+ | | 13 | 28 | 16 | 14.8 | 13.6 | 19.3 | 47.3 | ≧243 |
| | :NA | E. coli | 2 | 1.4 | 1.2 | 0.84 | 1 | 2.4 | 3.4 | 22.6 |
| | :Na+ | | 1 | 1.4 | 1.4 | 0.7 | ≦0.5 | 1.4 | 4 | 16 |
| | :K+ | | 3 | 1.3 | 1.1 | 0.8 | 1.3 | 2.2 | 5 | 10.1 |

TABLE XIII-continued

Antibacterial Activity of Chlorhexidine Digluconate in Combination with Nalidixic Acid (NA) or its Na+ and K+ Salts

| Drug Combinations | | Organism | No. of Strains | MIC (μg/ml)* Chlorhexidine:Nalidixate (%:%) | | | | | | |
|---|---|---|---|---|---|---|---|---|---|---|
| | | | | 100:0 | 95:5 | 75:25 | 50:50 | 25:75 | 5:95 | 0:100 |
| | :NA | K. pneumoniae | 3 | 8 | 3.6 | 4 | 3.2 | 3.2 | 5.7 | ≧40.1 |
| | :Na+ | | 3 | 8 | 3.2 | 5 | 1.4 | 2.8 | 5 | ≧50.3 |
| | :K+ | | 3 | 8 | 3.2 | 6.4 | 4 | 5 | 9 | ≧40.2 |
| | :NA | E. cloacae | 2 | 4 | 2 | 3.4 | 2.8 | 2.4 | 2.8 | 32 |
| | :Na+ | | 1 | 2 | 2 | 2 | 0.7 | 2 | 5.7 | 16 |
| | | | 1 | 11.3 | 8 | 5.7 | 1.4 | 2.8 | 8 | ≧125 |
| | :K+ | | 3 | 5.7 | 3.6 | 5 | 3.6 | 4 | 6.4 | ≧32 |
| | :NA | P. stuartii | 2 | 2.8 | 2 | 2.8 | 4.8 | 6.7 | 6.7 | 32 |
| | :Na+ | | 1 | 2.8 | 2.8 | 4 | 1 | 2.8 | 4 | 11.3 |
| | :K+ | | 2 | 2.8 | 2.4 | 4 | 4.8 | 8 | 9.6 | 16 |
| | :NA | S. marcescens | 2 | 16 | 6.7 | 6.7 | 5.7 | 8 | 2.4 | 11.3 |
| | :Na+ | | 1 | 32 | 11.3 | 11.3 | 8 | 5.7 | 4 | 11.3 |
| | :K+ | | 2 | 16 | 6.7 | 11.3 | 9.5 | 11.3 | 8 | 4.7 |
| | :NA | S. aureus | 3 | 1.7 | 0.7 | 0.7 | 0.7 | 1.6 | 5 | ≧177 |
| | :Na+ | | 1 | 0.7 | 1 | 0.5 | ≦0.35 | 2 | 11.3 | ≧125 |
| | :K+ | | 2 | 0.84 | 0.7 | 0.5 | 0.5 | 1 | 6.7 | ≧177 |
| | :NA | S. faecalis | 2 | 1.4 | 1 | 1 | 1 | 2.4 | 13.5 | ≧250 |
| | :Na+ | | 2 | 1.4 | 1.4 | 1 | ≦0.42 | 2.4 | 16 | ≧250 |
| | :K+ | | 2 | 1.4 | 1.2 | 1.4 | 1.4 | 3.4 | 13.5 | ≧250 |

*Geometric mean values (of combinations, where applicable) from 2 experiments.

TABLE XIV

Antibacterial Activity of Chlorhexidine Diacetate in Combination with Nalidixic Acid (NA) or its Na+ and K+ Salts

| Drug Combinations | | Organism | No. of Strains | MIC (μg/ml)* Chlorhexidine:Nalidixate (%:%) | | | | | | |
|---|---|---|---|---|---|---|---|---|---|---|
| | | | | 100:0 | 95:5 | 75:25 | 50:50 | 25:75 | 5:95 | 0:100 |
| Chlorhexidine Diacetate | :NA | P. aeruginosa | 2 | 3.4 | 4.8 | 3.4 | 1 | 8 | 22.6 | ≧250 |
| | | | 12 | 12 | 17.5 | 13.5 | 4 | 10.4 | 26.1 | ≧250 |
| | :Na+ | | 2 | 3.4 | 3.4 | 4.8 | 3.4 | 8 | 19 | ≧250 |
| | | | 9 | 12.7 | 33.2 | 17.3 | 10.5 | 13.7 | 25.4 | ≧250 |
| | :K+ | | 2 | 3.4 | 4.8 | 4.8 | 5.7 | 6.7 | 19 | ≧250 |
| | | | 10 | 12.1 | 21.1 | 14.4 | 13.5 | 13.9 | 19.7 | ≧250 |
| | :NA | E. coli | 3 | 0.5 | 0.4 | 0.6 | 0.5 | 1.3 | 4 | 10.1 |
| | :Na+ | | 3 | 0.5 | 0.7 | 0.6 | 0.5 | 1.1 | 3.2 | 5.7 |
| | :K+ | | 3 | 0.5 | 0.5 | 0.6 | 0.6 | 1.1 | 2.8 | 4 |
| | :NA | K. pneumoniae | 2 | 1.7 | 2.8 | 4 | 1.4 | 2.4 | 5.7 | 11.3 |
| | | | 1 | 2 | 2.8 | 5.7 | 1.4 | 4 | 8 | 63 |
| | :Na+ | | 3 | 1.8 | 2.8 | 3.6 | 4 | 4 | 4.5 | 8 |
| | :K+ | | 3 | 1.8 | 4 | 2.8 | 3.6 | 4 | 4.5 | 16 |
| | :NA | E. cloacae | 2 | 1.2 | 1.7 | 4 | 0.7 | 2 | 4.8 | 11.3 |
| | | | 1 | 2 | 5.7 | 5.7 | 1 | 2.8 | 5.7 | ≧177 |
| | :Na+ | | 3 | 1.4 | 2.8 | 2.5 | 2.2 | 3.2 | 3.6 | 12.7 |
| | :K+ | | 2 | 1.2 | 2.8 | 1.7 | 2.4 | 2.4 | 2.8 | 8 |
| | | | 1 | 2 | 8 | 4 | 4 | 4 | 4 | 44.9 |
| | :NA | P. stuartii | 2 | 2 | 2 | 2.8 | 2 | 5.7 | 11.3 | 22.6 |
| | :Na+ | | 1 | 2.8 | 4 | 5.7 | 8 | 5.7 | 11.3 | 5.7 |
| | :K+ | | 1 | 1.4 | 2 | 2 | 2 | 5.7 | 11.3 | 11.3 |
| | :NA | S. marcescens | 1 | 2 | 5.7 | 5.7 | 1.4 | 4 | 11.3 | 5.7 |
| | | | 1 | 11.3 | 22.6 | 16 | 2.8 | 4 | 11.3 | 5.7 |
| | :Na+ | | 1 | 2 | 5.7 | 4 | 4 | 5.7 | 8 | 2.8 |
| | | | 1 | 11.3 | 44.9 | 11.3 | 5.7 | 8 | 8 | 2.8 |
| | :K+ | | 1 | 2 | 11.3 | 4 | 5.7 | 5.7 | 11.3 | 2 |
| | | | 1 | 11.3 | 44.9 | 16 | 8 | 8 | 11.3 | 1.4 |
| | :NA | S. aureus | 3 | 0.5 | 0.35 | 0.5 | 0.6 | 1 | 3.2 | ≧177 |
| | :Na+ | | 3 | 0.5 | 0.8 | 0.6 | 0.6 | 0.6 | 3.6 | 88.7 |
| | :K+ | | 3 | 0.5 | 0.6 | 0.7 | 0.7 | 1.1 | 2.8 | ≧88.9 |
| | :NA | S. faecalis | 2 | 0.5 | 0.5 | 0.6 | 0.6 | 1 | 4.8 | ≧250 |
| | :Na+ | | 2 | 0.5 | 0.7 | 0.5 | 0.5 | 1 | 5.7 | ≧250 |
| | :K+ | | 2 | 0.5 | 0.5 | 0.8 | 0.6 | 1.2 | 4 | ≧250 |

*Geometric mean values (of combinations, where applicable) from 2 experiments.

TABLE XV

Antibacterial Activity of Chlorhexidine Hydrochloride in Combination with Nalidixic Acid (NA) or its Na+ and K+ Salts

| Drug Combinations | | Organism | No. of Strains | MIC (μg/ml)* Chlorhexidine:Nalidixate (%:%) | | | | | | |
|---|---|---|---|---|---|---|---|---|---|---|
| | | | | 100:0 | 95:5 | 75:25 | 50:50 | 25:75 | 5:95 | 0:100 |
| Chlorhexidine Hydrochloride | :NA | P. aeruginosa | 5 | 67.5 | 42 | 95 | 88.7 | ≧177 | 109 | ≧250 |
| | | | 9 | ≧250 | 54.2 | 103.3 | 88.7 | ≧177 | 103.3 | ≧250 |
| | :Na+ | | 4 | 68.6 | 114.7 | 81.5 | 74.8 | ≧250 | 250 | ≧250 |

TABLE XV-continued

Antibacterial Activity of Chlorhexidine Hydrochloride in Combination with Nalidixic Acid (NA) or its Na+ and K+ Salts

| Drug Combinations | | Organism | No. of Strains | MIC (μg/ml)* Chlorhexidine:Nalidixate (%:%) | | | | | | |
|---|---|---|---|---|---|---|---|---|---|---|
| | | | | 100:0 | 95:5 | 75:25 | 50:50 | 25:75 | 5:95 | 0:100 |
| | | | 9 | ≧250 | 107.4 | 66.2 | 58.4 | ≧250 | 223 | ≧250 |
| | :K+ | | 5 | 67.5 | 51.4 | 63 | 88.7 | 58.9 | 95 | ≧233 |
| | | | 8 | ≧250 | 60.4 | 74.8 | 88.7 | 57.9 | 125 | ≧229 |
| | :NA | E. coli | 3 | 2.8 | 2.5 | 6.4 | 3.6 | 10.1 | 5 | 20.2 |
| | :Na+ | | 3 | 2.8 | 3.2 | 2 | 6.4 | 3.2 | 2.8 | 16 |
| | :K+ | | 2 | 3.4 | 8 | 5.7 | 2.8 | 1.4 | 8 | 13.5 |
| | :NA | K. pneumoniae | 3 | 44.9 | 3.2 | 11.3 | 4.5 | 11.3 | 10.1 | 20.2 |
| | :Na+ | | 3 | 44.9 | 5 | 6.4 | 6.4 | 7.1 | 7.1 | 22.6 |
| | :K+ | | 2 | 37.9 | 11.3 | 5.7 | 3.1 | 1.7 | 6.7 | 16 |
| | | | 1 | 63 | 8 | 5.7 | 11.3 | 4 | 22.6 | 125 |
| | :NA | E. cloacae | 1 | 16 | 1.4 | 2 | 4 | 4 | 5.7 | 44.9 |
| | | | 2 | ≧250 | 9.5 | 13.5 | 9.5 | 37.9 | 26.9 | 32 |
| | :Na+ | | 2 | ≧250 | 5.7 | 8 | 5.7 | 9.5 | 8 | 37.9 |
| | :K+ | | 1 | 16 | 8 | 2.8 | 4 | 1 | 8 | 16 |
| | | | 2 | ≧250 | 16 | 6.7 | 4.8 | 2.8 | 19 | 37.9 |
| | :NA | P. stuartii | 2 | 32 | 22.6 | 9.5 | 8 | 9.5 | 3.4 | 32 |
| | :Na+ | | 2 | 32 | 13.5 | 13.5 | 6.7 | 4.8 | 6.7 | 6.7 |
| | :K+ | | 2 | 32 | 16 | 11.3 | 6.7 | 1.4 | 8 | 11.3 |
| | :NA | S. marcescens | 1 | 63 | 16 | 8 | 4 | 8 | 4 | 4 |
| | | | 1 | ≧250 | 16 | 16 | 4 | 8 | 4 | 2.8 |
| | :Na+ | | 1 | 63 | 4 | 8 | 4 | 2 | 2 | 11.3 |
| | | | 1 | ≧250 | 16 | 8 | 4 | 2 | 2.8 | 11.3 |
| | :K+ | | 1 | ≧250 | 63 | 11.3 | 2 | 1 | 2.8 | 2.8 |
| | :NA | S. aureus | 3 | 3.6 | 4 | 4 | 6.4 | 11.3 | 44.9 | 125 |
| | :Na+ | | 2 | 4 | 2.8 | 1.2 | 5.7 | 16 | 5.7 | 88.7 |
| | :K+ | | 3 | 3.6 | 4 | 4.5 | 10.1 | 9 | 35.8 | 99.5 |
| | :NA | S. faecalis | 2 | 2.8 | 5.7 | 11.3 | 8 | ≧177 | 125 | ≧250 |
| | :Na+ | | 1 | 2.8 | 32 | 4 | 8 | ≧125 | 16 | ≧250 |
| | :K+ | | 2 | 2.8 | 9.5 | 8 | 8 | 44.9 | 63 | ≧250 |

*Geometric mean values (of combinations, where applicable) from 2 experiments.

TABLE XVI

Antibacterial Activity of Chlorhexidine Digluconate in Combination with Phosphanilic Acid (PA) or its Na+ and K+ Salts

| Drug Combinations | | Organism | No. of Strains | MIC (μg/ml)* Chlorhexidine:Phosphanilate (%:%) | | | | | | |
|---|---|---|---|---|---|---|---|---|---|---|
| | | | | 100:0 | 95:5 | 75:25 | 50:50 | 25:75 | 5:95 | 0:100 |
| Chlorhexidine | :PA | P. aeruginosa | 10 | 17.8 | 5.2 | 3 | 1.9 | 1.5 | 2.3 | 1.9 |
| Digluconate | :Na+ | | 10 | 17.8 | 7.9 | 4.1 | 3.4 | 5.1 | 2.9 | 2.3 |
| | :K+ | | 10 | 17.5 | 8.9 | 4.7 | 3.9 | 3 | 3.3 | 3.7 |
| | :PA | E. coli | 3 | 0.4 | 0.5 | 0.5 | 0.5 | 1.2 | 6.4 | ≧184 |
| | :Na+ | | 3 | 0.4 | 0.5 | 0.5 | 0.8 | 0.6 | 6.9 | ≧170 |
| | :K+ | | 3 | 0.4 | 0.5 | 0.4 | 0.9 | 0.6 | 7.4 | ≧157 |
| | :PA | K. pneumoniae | 3 | 3.6 | 2.4 | 2.8 | 4.5 | 5 | 67 | ≧177 |
| | :Na+ | | 3 | 3.4 | 2.5 | 4 | 5.3 | 6.7 | 84 | ≧187 |
| | :K+ | | 3 | 3.6 | 3 | 3.8 | 5.7 | 8.5 | 48 | ≧177 |
| | :PA | E. cloacae | 3 | 2.7 | 2 | 2.1 | 3.6 | 4.2 | 45 | ≧132 |
| | :Na+ | | 3 | 2.7 | 2.2 | 3.4 | 4.8 | 6.4 | 50 | ≧149 |
| | :K+ | | 3 | 2.7 | 2.4 | 3.2 | 4.5 | 9.5 | 56 | ≧177 |
| | :PA | P. stuartii | 2 | 1.5 | 1.4 | 1.7 | 1.7 | 1.5 | 3.7 | 5.7 |
| | :Na+ | | 2 | 1.5 | 1.5 | 2.2 | 2.6 | 3.1 | 5.7 | 9.5 |
| | :K+ | | 2 | 1.5 | 2 | 2.2 | 2.4 | 2.6 | 6.2 | 9 |
| | :PA | S. marcescens | 2 | 8.7 | 3.1 | 2.2 | 1.3 | 1 | 1 | 0.8 |
| | :Na+ | | 2 | 8.7 | 3.7 | 2.8 | 2.8 | 2 | 1.4 | 0.9 |
| | :K+ | | 2 | 8.7 | 4.8 | 2.8 | 2.8 | 1.7 | 1.8 | 1.7 |
| | :PA | S. aureus | 3 | 0.3 | 0.4 | 0.3 | 0.4 | 0.7 | 5.4 | ≧158 |
| | :Na+ | | 3 | 0.3 | 0.5 | 0.4 | 0.5 | 1.7 | 4.3 | ≧158 |
| | :K+ | | 3 | 0.3 | 0.4 | 0.3 | 0.5 | 0.9 | 5 | ≧184 |
| | :PA | S. faecalis | 2 | 0.6 | 0.6 | 0.6 | 0.8 | 2 | 9 | ≧198 |
| | :Na+ | | 2 | 0.6 | 0.6 | 0.9 | 1 | 3.2 | 9 | ≧250 |
| | :K+ | | 2 | 0.6 | 0.6 | 0.6 | 0.7 | 1.8 | 11.3 | ≧250 |

*Geometric mean values (of combinations, where applicable) from 3 to 5 experiments.

TABLE XVII

Antibacterial Activity of Chlorhexidine Diacetate in Combination with Phosphanilic Acid (PA) or its Na+ and K+ Salts

| Drug Combinations | | Organism | No. of Strains | MIC (μg/ml)* Chlorhexidine:Phosphanilate (%:%) | | | | | | |
|---|---|---|---|---|---|---|---|---|---|---|
| | | | | 100:0 | 95:5 | 75:25 | 50:50 | 25:75 | 5:95 | 0:100 |
| Chlorhexidine | :PA | P. aeruginosa | 6 | 13.7 | 18 | 7.4 | 5.2 | 7.7 | 3.6 | 1.7 |
| Diacetate | :Na+ | | 1 | 2.5 | 4 | 4 | 6.4 | 8 | 8 | 32 |

TABLE XVII-continued

Antibacterial Activity of Chlorhexidine Diacetate in Combination with Phosphanilic Acid (PA) or its Na+ and K+ Salts

| Drug Combinations | Organism | No. of Strains | MIC (µg/ml)* Chlorhexidine:Phosphanilate (%:%) | | | | | | |
|---|---|---|---|---|---|---|---|---|---|
| | | | 100:0 | 95:5 | 75:25 | 50:50 | 25:75 | 5:95 | 0:100 |
| | | 7 | 14.5 | 17.1 | 7 | 5.9 | 3.6 | 3.2 | 1.3 |
| :K+ | | 1 | 2.5 | 1.6 | 4 | 5 | 16 | 32 | 40.1 |
| | | 7 | 14.5 | 20.8 | 11.9 | 7.3 | 7 | 7.5 | 1.7 |
| :PA | E. coli | 2 | 0.8 | 0.9 | 1.2 | 1.6 | 2.3 | 11.3 | 125 |
| :Na+ | | 2 | 0.8 | 0.5 | 0.9 | 0.9 | 2.1 | 9.2 | ≧154 |
| :K+ | | 2 | 0.8 | 0.5 | 0.8 | 1.1 | 3 | 11.3 | ≧89 |
| :PA | K. pneumoniae | 2 | 3.5 | 3.5 | 4.9 | 5.7 | 11.3 | 59 | ≧89 |
| :Na+ | | 2 | 4 | 4 | 7.3 | 8 | 19 | 82 | ≧193 |
| :K+ | | 2 | 3.5 | 2.8 | 4.6 | 10.6 | 18.3 | 59 | ≧102 |
| :PA | E. cloacae | 3 | 2.9 | 6.1 | 6.1 | 7.3 | 13.3 | ≧76 | ≧165 |
| :Na+ | | 3 | 3.6 | 3.8 | 6 | 4 | 18 | 167 | ≧210 |
| :K+ | | 3 | 2.9 | 3.3 | 4.4 | 7.3 | 16.8 | 79 | ≧150 |
| :PA | P. stuartii | 1 | 2.6 | 5.3 | 5.3 | 4.6 | 4.6 | 9.2 | 7 |
| :Na+ | | 1 | 2.6 | 3 | 3.5 | 4.6 | 4 | 8 | 12.1 |
| :K+ | | 1 | 2.6 | 2.3 | 3 | 3.5 | 10.6 | 14 | 10.6 |
| :PA | S. marcescens | 2 | 13 | 13 | 4.6 | 5.3 | 3 | 3.3 | 1.4 |
| :Na+ | | 2 | 16 | 26.9 | 6.7 | 5.2 | 2.4 | 3.1 | 1.1 |
| :K+ | | 2 | 13 | 21.1 | 7.5 | 5.7 | 6.1 | 7.5 | 5.7 |
| :PA | S. aureus | 3 | 0.4 | 0.6 | 0.8 | 0.9 | 1.7 | 6.4 | ≧75 |
| :Na+ | | 3 | 0.4 | 0.4 | 0.5 | 0.6 | 1.2 | 4.8 | ≧140 |
| :K+ | | 3 | 0.4 | 0.4 | 0.6 | 0.8 | 1.7 | 7.1 | ≧79 |
| :PA | S. faecalis | 2 | 0.8 | 0.8 | 1.5 | 2.1 | 3 | 13.9 | ≧250 |
| :Na+ | | 2 | 0.8 | 0.8 | 1.2 | 1.2 | 2.6 | 14.9 | ≧250 |
| :K+ | | 2 | 0.8 | 0.7 | 1.2 | 1.6 | 4.3 | 11.3 | ≧165 |

*Geometric mean values (of combinations, where applicable) from 3 to 5 experiments.

TABLE XVIII

Antibacterial Activity of Chlorhexidine Hydrochloride in Combination with Phosphanilic Acid (PA) or its Na+ and K+ Salts

| Drug Combinations | Organism | No. of Strains | MIC (µg/ml)* Chlorhexidine:Phosphanilate (%:%) | | | | | | |
|---|---|---|---|---|---|---|---|---|---|
| | | | 100:0 | 95:5 | 75:25 | 50:50 | 25:75 | 5:95 | 0:100 |
| Chlorhexidine Hydrochloride :PA | P. aeruginosa | 2 | 24.2 | 24.2 | 21.1 | 26 | 39.2 | 51.4 | ≧59 |
| | | 8 | ≧125 | 14.9 | 5.1 | 2.8 | 2.4 | 1.9 | 2.3 |
| :Na+ | | 1 | 36.6 | 27.9 | 27.9 | 27.9 | 42 | 48.1 | 55 |
| | | 7 | ≧105 | 21.5 | 8 | 4.6 | 3.6 | 2.2 | 2.8 |
| :K+ | | 1 | 36.6 | 21.1 | 42 | 42 | 32 | 36.6 | 32 |
| | | 6 | ≧125 | 27.9 | 9.6 | 6.2 | 2.8 | 2.4 | 2.5 |
| :PA | E. coli | 3 | 2.8 | 2.4 | 3 | 5 | 12.7 | ≧63 | ≧181 |
| :Na+ | | 2 | 2.8 | 3.4 | 6.2 | 11.3 | 27 | 89 | ≧149 |
| :K+ | | 3 | 2.8 | 2.8 | 7 | 7 | 10.6 | 32 | ≧165 |
| :PA | K. pneumoniae | 3 | 23.2 | 37.9 | 25.4 | ≧40 | ≧75 | ≧140 | ≧149 |
| :Na+ | | 3 | 32 | 25.4 | 30.2 | ≧89 | ≧132 | 223 | ≧223 |
| :K+ | | 3 | 23.2 | 45.9 | ≧42 | ≧40 | ≧87 | 181 | ≧190 |
| :PA | E. cloacae | 1 | 16 | 20.2 | 10.1 | 20.2 | 50.3 | ≧250 | ≧250 |
| :Na+ | | 1 | 10.6 | 7 | 16 | 32 | ≧63 | 144 | ≧250 |
| :K+ | | 1 | 10.6 | 9.2 | ≧21.1 | ≧42 | ≧72 | 144 | ≧218 |
| :PA | P. stuartii | 2 | 14.7 | 14.7 | 7.3 | 9.5 | 12.3 | 13.5 | 16 |
| :Na+ | | 2 | 14.9 | 9.9 | 11.3 | 11.3 | 9.9 | 10.6 | 14.9 |
| :K+ | | 2 | 14.7 | 16 | 10.4 | 12.3 | 8 | 10.4 | 20.8 |
| :PA | S. marcescens | 1 | 24.3 | 10.6 | 5.3 | 3.5 | 3 | 3 | 2.6 |
| | | 1 | ≧165 | 10.6 | 5.3 | 3.5 | 2.3 | 2.6 | 2.3 |
| :Na+ | | 1 | 26.9 | 11.3 | 8 | 5.7 | 5.7 | 3.4 | 2.8 |
| :K+ | | 1 | 24.3 | 18.4 | 13.9 | 9.2 | 5.3 | 4 | 3 |
| | | 1 | ≧165 | 24.3 | 13.9 | 8 | 4 | 3 | 5.3 |
| :PA | S. aureus | 3 | 2.4 | 2.4 | 1.9 | 3.8 | 9 | 35.8 | ≧149 |
| :Na+ | | 2 | 2.3 | 1.6 | 3.3 | 4.9 | 8 | 45 | ≧150 |
| :K+ | | 3 | 2.1 | 2.8 | 3.4 | 4.8 | 6.7 | 22.6 | ≧198 |
| :PA | S. faecalis | 2 | 4 | 2.8 | 4.4 | 7.3 | 19 | 97 | ≧250 |
| :Na+ | | 2 | 4 | 3.5 | 6.1 | 9.9 | 17.2 | 89 | ≧250 |
| :K+ | | 2 | 2.8 | 3.4 | 8 | 10.4 | 13.5 | 49 | ≧210 |

*Geometric mean values (of combinations, where applicable) from 3 to 5 experiments.

TABLE XIX

Mean Synergism Indices Against Bacteria of Chlorhexidine Salts in Combination with Nalidixic Acid or Its Salts

| Chemical Combinations | Mean Synergism Index Chlorhexidine:Nalidixate (%:%) | | | | |
|---|---|---|---|---|---|
| | 95:5 | 75:25 | 50:50 | 25:75 | 5:95 |
| Chlorhexidine digluconate with | .54 | .49 | .42 | .39 | .60 |
| Nalidixic Acid | | | | | |

TABLE XIX-continued

Mean Synergism Indices Against Bacteria of Chlorhexidine Salts in Combination with Nalidixic Acid or Its Salts

| Chemical Combinations | Mean Synergism Index Chlorhexidine:Nalidixate (%:%) | | | | |
|---|---|---|---|---|---|
| | 95:5 | 75:25 | 50:50 | 25:75 | 5:95 |
| Chlorhexidine digluconate with Sodium nalidixate | .79 | .58 | .21 | .30 | .37 |
| Chlorhexidine digluconate with Potassium nalidixate | .67 | .71 | .57 | .66 | .59 |
| Chlorhexidine diacetate with Nalidixic acid | 1.49 | 1.51 | .40 | .59 | .74 |
| Chlorhexidine diacetate with Sodium nalidixate | 1.98 | 1.31 | .99 | .99 | 1.12 |
| Chlorhexidine diacetate with Potassium nalidixate | 2.39 | 1.45 | 1.23 | 1.20 | 1.60 |
| Chlorhexidine hydrochloride with Nalidixic acid | .57 | .92 | .58 | 2.22 | .79 |
| Chlorhexidine hydrochloride with Sodium nalidixate | 1.46 | .34 | .57 | 1.70 | .49 |
| Chlorhexidine hydrochloride with Potassium nalidixate | .47 | .71 | .57 | .73 | .65 |

TABLE XX

Mean Synergism Indices Against Bacteria of Chlorhexidine Salts in Combination with Phosphanilic Acid or Its Salts

| Chemical Combination | Mean Synergism Index Chlorhexidine:Phosphanilate (%:%) | | | | |
|---|---|---|---|---|---|
| | 95:5 | 75:25 | 50:50 | 25:75 | 5:95 |
| Chlorhexidine digluconate with Phosphanilic Acid | .83 | .74 | .68 | .62 | 1.01 |
| Chlorhexidine digluconate with Sodium phosphanilate | .92 | .97 | .99 | 1.07 | 1.10 |
| Chlorhexidine digluconate with Potassium phosphanilate | .95 | .79 | .85 | .69 | .97 |
| Chlorhexidine diacetate with Phosphanilic acid | 1.45 | 1.38 | 1.33 | 1.38 | 1.44 |
| Chlorhexidine diacetate with Sodium phosphanilate | 1.30 | 1.26 | 1.23 | 1.14 | 1.44 |
| Chlorhexidine diacetate with Potassium phosphanilate | 1.05 | 1.16 | 1.17 | 1.58 | 1.59 |
| Chlorhexidine hydrochloride with Phosphanilic acid | .85 | .66 | .78 | .97 | 1.17 |
| Chlorhexidine hydrochloride with Sodium phosphanilate | .73 | 1.00 | 1.20 | 1.31 | 1.21 |
| Chlorhexidine Hydrochloride with Potassium phosphanilate | .99 | 1.34 | 1.30 | 1.05 | .95 |

What is claimed is:

1. The compound chlorhexidine diphosphanilate.
2. An antibacterial composition comprising an effective amount of the compound chlorhexidine diphosphanilate and a pharmaceutically acceptable carrier.
3. The composition of claim 2, wherein the compound is present in an amount of from about 0.1 to 10 percent by weight, based on the total composition weight.
4. The composition of claim 2, wherein the compound is present in an amount of from about 0.25 to 5.0 percent by weight, based on the total composition weight.
5. The composition of claim 2, wherein the compound is present in an amount of from about 0.75 to 2.5 percent by weight, based on the total composition weight.

* * * * *